United States Patent [19]

Pelton

[11] 4,055,188

[45] Oct. 25, 1977

[54] THERAPEUTIC WRAP

[75] Inventor: Robert J. Pelton, Santa Ana, Calif.

[73] Assignee: Divajex, Santa Ana, Calif.

[21] Appl. No.: 656,705

[22] Filed: Feb. 9, 1976

[51] Int. Cl.² ........................... A61F 7/00; A61F 7/04
[52] U.S. Cl. ..................................... 128/402; 128/403
[58] Field of Search ............... 128/399, 403, 379, 382, 128/402

[56] References Cited

U.S. PATENT DOCUMENTS

| 3,587,578 | 6/1971 | Walker | 128/402 |
| 3,643,665 | 2/1972 | Caillouette | 128/403 |
| 3,871,376 | 3/1975 | Kozak | 128/403 |
| 3,882,873 | 5/1975 | Arango | 128/379 |
| 3,885,403 | 5/1975 | Spencer | 128/403 |
| 3,893,834 | 7/1975 | Armstrong | 128/403 |
| 3,900,035 | 8/1975 | Welch et al. | 128/402 |

Primary Examiner—Lawrence W. Trapp
Attorney, Agent, or Firm—Gordon L. Peterson

[57] ABSTRACT

A therapeutic wrap comprising an elongated, flexible, resilient bandage and a refrigerant gel package carried by the bandage.

5 Claims, 7 Drawing Figures

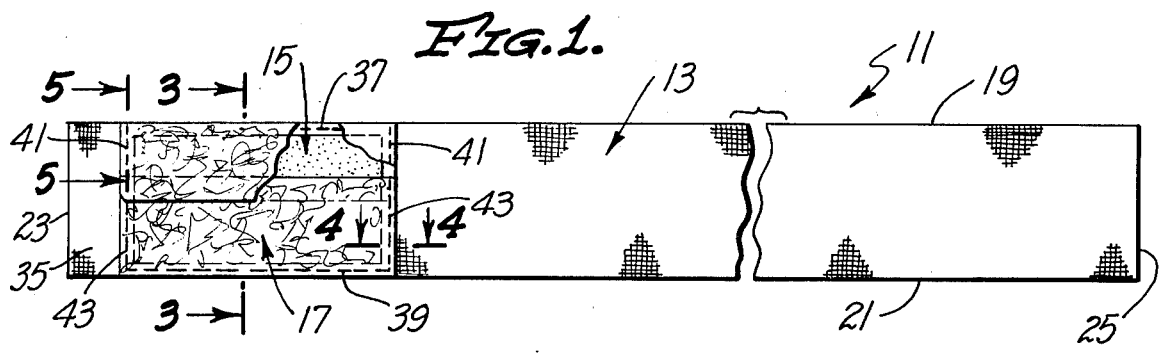
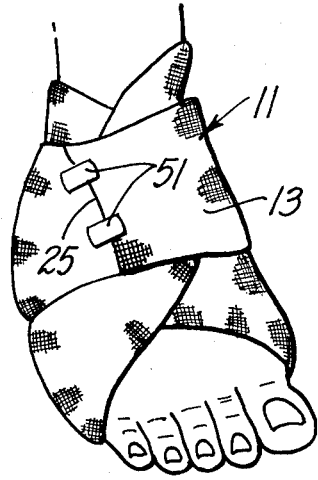
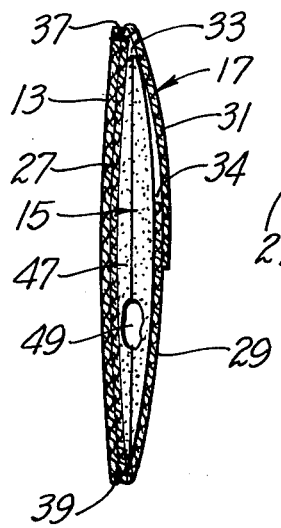
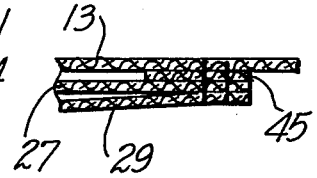
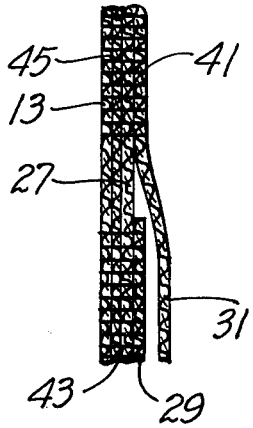
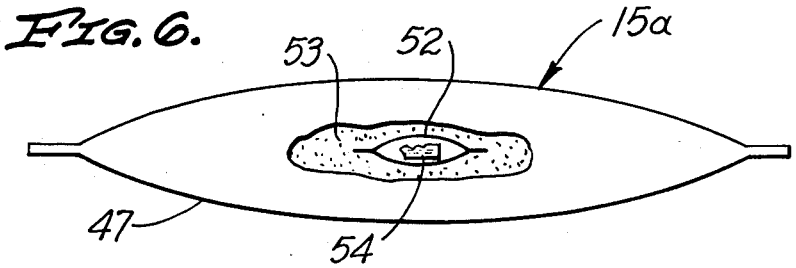
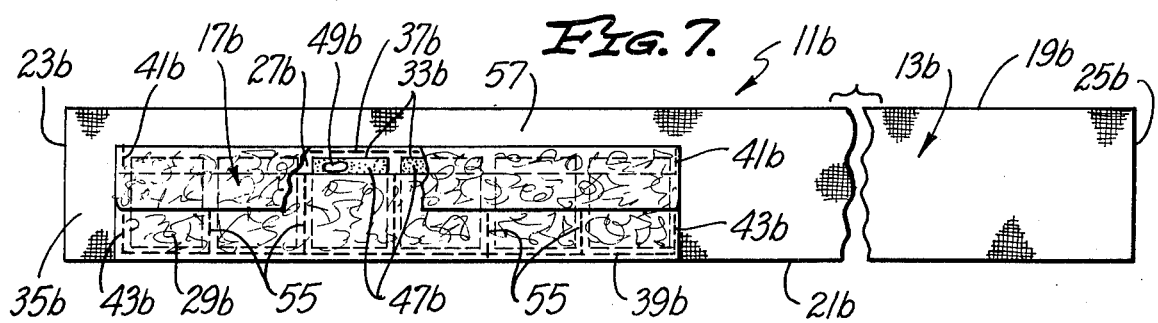

THERAPEUTIC WRAP

BACKGROUND OF THE INVENTION

Various injuries, such as certain athletic injuries, are commonly treated by wrapping an elastic bandage around the injured region. The elastic bandage aids the injured region by supporting it and by applying compressive forces to it.

Certain athletic injuries are also commonly treated by adding heat to, or removing heat from, the injured region. Heat removal can be accomplished in many different ways such as by applying cold packs which include ice, refrigerant gel, or materials which react endothermically. Heat can be added in various ways such as by applying a hot pack which includes materials capable of reacting exothermically or by using an electric heating pad.

The prior art includes a cold wrap usable to apply refrigerant gel to an injured region; however, this cold wrap does not provide the desired compressive forces to the injured region. It is also known to apply ice to an injured region by wrapping the ice and an elastic bandage around the injured region. However, the use of this procedure is greatly limited by the mess created by the melting ice.

SUMMARY OF THE INVENTION

The present invention provides a single therapeutic wrap which obtains the advantages of support, compressive loading, and cooling. With this invention, cooling is obtained by carrying a refrigerant gel package on an elongated, flexible resilient strip. After cooling the refrigerant gel, the flexible strip can be wrapped around the injured region. The flexible strip provides support and compressive loading for the injured region and the refrigerant gel provides the cooling.

The elongated flexible strip may take the form of an elastic bandage. The bandage is preferably resilient in the direction in which it is elongated.

The refrigerant gel package may include refrigerant gel and container means for containing the refrigerant gel therein. Refrigerant gel has a very high specific heat and a very high heat of fusion. Refrigerant gel can be readily packaged and reused, and it does not liquefy when its temperature exceeds its freezing point, i.e. that temperature where a quantity of heat energy is transferred without any resultant change in temperature due to a change of state. Refrigerant gel is commercially available from Divajex of Santa Ana, California, and is disclosed, by way of example, in U.S. Pat. No. 2,803,115.

Refrigerant gel is superior to many other materials which could be utilized for heat removal purposes. For example, refrigerant gel is not injurious to the skin so a rupture of the container means would not be harmful to the user. The refrigerant gel package will not drip as its temperature increases. In addition, refrigerant gels are available which remain pliable even when the temperature of the gel is reduced to 5° Fahrenheit.

The refrigerant gel package can be advantageously carried on the bandage by carrying means which includes at least one pocket. The pocket is preferably openable to permit removal of the refrigerant gel package. This permits the elastic bandage to be used in a conventional manner without the refrigerant gel when desired. Removal of the refrigerant gel from the elastic bandage also facilitates cooling of the same in a refrigerator or freezer.

It is desirable to provide insulation between the refrigernat gel package and the injured region on which the wrap is used. The insulation can advantageously be provided as a part of the pocket.

Although the pocket may be attached to the bandage in various ways, stitching or sewing of at least a portion of the pocket to the bandage can be accomplished quickly and inexpensively. The pocket can be constructed of various materials. However, a flexible material which will provide some insulating effect to prevent making the injured region too cold is preferred.

The pocket is perferably no wider than about the width of the bandage. Although the pocket could be wider than the bandage, its edges would then protrude beyond the bandage and this would provide a less attractive therapeutic wrap. In addition, to the extent that the pocket extends beyond the side edges of the bandage, no compressive force would be available at those regions.

The pocket may have one or more compartments. If one relatively large compartment is provided, then it will usually be desirable to employ the kind of refrigerant gel which does not solidify when its temperature is dropped well below the freezing point of water. Multiple compartments can be used to advantage when it is desired to use refrigerant gel or other material which freezes solid. By using multiple relatively small compartments arranged along the length of the bandage, the presence of the rigid refrigerant gel does not prevent the therapeutic wrap from being wound around the injured region because the therapeutic wrap forms, in effect, hinges between the adjacent compartments. One advantage of this arrangement is that the gel which becomes rigid stays cold longer. In addition, greater quantities of the gel can be used because the hinges allow it to be wrapped around an injured region easier than wrapping a large pliable gel package. Multiple compartments also provide flexibility in that some or all of the compartments can be used to contain the refrigerant gel, and this is also beneficial in terms of getting the heat removal action at the desired region. The multiple compartment therapeutic wrap is particularly adapted for larger areas of the body such as shoulders, hips and back.

Another feature of the invention is that a material for adding heat can be placed in the pocket. For example, chemicals which react exothermically can be used.

The invention, together with further features and advantages thereof, can best be understood by reference to the following description taken in connection with the accompanying illustrative drawing.

BRIEF DESCRIPTION OF THE DRAWING

FIG. 1 is a plan view of a therapeutic wrap constructed in accordance with the teachings of this invention with a portion of the pocket being broken away.

FIG. 2 is a perspective view showing the therapeutic wrap in use.

FIG. 3 is an enlarged sectional view taken generally along line 3—3 of FIG. 1.

FIG. 4 is an enlarged, fragmentary sectional view taken generally along line 4—4 of FIG. 1.

FIG. 5 is an enlarged, fragmentary sectional view taken generally along line 5—5 of FIG. 1.

FIG. 6 is a side elevational view of a hot pack, with parts broken away, which can be used with the bandage of FIGS. 1-5.

FIG. 7 is a plan view of a second embodiment of therapeutic wrap constructed in accordance with the teachings of this invention and with a portion of the pocket broken away.

DESCRIPTION OF THE PREFERRED EMBODIMENT

FIG. 1 shows a therapeutic wrap 11 which generally includes a bandage 13, heat removal means in the form of a refrigerant gel package 15, and a pocket 17 for carrying the refrigerant gel package on the bandage 13. A hot pack for adding heat may be used in lieu of the refrigerant gel package 15. The bandage 13 is in the form of an elongated flexible strip which is resilient in the direction of its elongation. The bandage 13 may be an elastic cloth bandage of conventional construction. The bandage 13 in the embodiment illustrated is rectangular and has side edges 19 and 21 and end edges 23 and 25. The pocket 17 can be of various different constructions, and in the embodiment illustrated it includes a back wall 27 (Fig. 3), a front wall 29 integrally joined to the back wall, and a front flap 31 integrally joined to the back wall and overlapping an upper edge portion of the front wall. The pocket 17 has a single, relatively large compartment 33 therein. The pocket 17 can be opened to provide access to the compartment 33 through an opening 34 in the front wall 29 by lifting the lower edge of the front flap 31.

In the embodiment illustrated, the pocket 17 is adjacent the end edge 23. The left edge (as viewed in FIG. 1) of the pocket 17 is spaced inwardly from the end edge 23 to provide a relatively narrow gripping section 35. The pocket 17 in the embodiment illustrated is of approximately the same width as the bandage 13 and the longitudinal edges of the pocket generally coincide with the side edges 19 and 21, respectively, of the bandage 13. By way of example, the gripping section 35 may be of the order of one to two inches in width, and the pocket 17 may be remotely located relative to the end edge 25.

The pocket 17 may be attached to the bandage 13 in various ways. In the form shown in FIGS. 1-4, the pocket is attached to the bandage 13 by stitching which extends along an upper seam 37, a lower seam 39, upper side seams 41 and lower side seams 43. The stitches along the upper seams 37 extend through the back wall 27 and the bandage 13 and along substantially the full length of the upper edge portion of the pocket 17. The stitching along the lower seam 39 extends through the front wall 29, the back wall 27, and the bandage 13 and along substantially the full length of the lower edge portion of the pocket 17.

Reinforcing material in the form of reinforcing tape 45 (FIGS. 3A and 4) lies between the back wall 27 and the bandage 13 along the side seams 41 and 43. The stitches along the upper side seams 41 extend through the flap 31, the back wall 27, the tape 45, and the bandage 13. The upper side seam 41 terminates above the upper edge of the front wall 29 to allow the flap 31 to be opened sufficiently to insert and remove the refrigerant gel package 15. The upper side seams 41 prevent the flap 31 from opening the pocket 17 inadvertently to allow the refrigerant gel package 15 to fall out of the pocket.

The stitching along the lower side seams 43 extends through the front wall 29, the back wall 27, the reinforcing tape 45, and the bandage 13. If desired, the reinforcing tape 45 can also be provided along the upper seam 37 and the lower seam 39.

The refrigerant gel package 15 includes container means in the form of a flexible, sealed, plastic bag or container 47 and refrigerant gel 49 within the container. The refrigerant gel 49 in the embodiment of FIGS. 1-5 is preferably of the type which remains pliable at temperatures as low as 5° Fahrenheit. The container 47 is sealed so that none of the gel can escape.

In use, the refrigerant gel package 15 is removed from the pocket 17 and cooled to the desired temperature which may be as low as 5° Fahrenheit. The cooled refrigerant gel package 15 is reinserted into the compartment 33. The user then grips the therapeutic wrap 11 at the gripping section 35 and along another region of the bandage 13 and wraps the therapeutic wrap around the injured region being careful to place the refrigerant gel package 15 contiguous the injured region. As shown in FIG. 2, if the injured region is an ankle, the therapeutic wrap 11 may be applied to the ankle and foot as shown in FIG. 2. The end edge 25 of the bandage 13 is then attached to another portion of the bandage using conventional clips 51. Consequently, the injured ankle receives the necessary cooling action and compression.

Alternatively a hot pack 15a (FIG. 6) can be used in the pocket 17 in lieu of the refrigerant gel package 15. The hot pack 15a may be of the commercially available type and include a flexible, plastic outer container 47, a rupturable, flexible inner container 52, and exothermic materials 53 and 54 within the containers 47 and 52, respectively. The inner container 52 can be ruptured with a blow to cause the exothermic materials to mix and give off heat.

FIG. 7 shows a therapeutic wrap 11b which is identical to the therapeutic wrap 11 in all respects not specifically shown or described herein. Portions of the therapeutic wrap 11b corresponding to portions of the therapeutic wrap 11 are designated by corresponding reference numerals followed by the letter "b."

The primary difference between the therapeutic wrap 11b and the therapeutic wrap 11 is that the pocket 17b is divided into a plurality of compartments 33b and the container means for the refrigerant gel is divided into a corresponding number of containers 47b. In addition, the refrigerant gel 49b may be of the type which becomes solid and nonpliable at temperatures about 32° F.

As shown in FIG. 7, the pocket 17b is divided into a plurality of the compartments 33b by stitching extending along intermediate seams 55. The stitching along the intermediate seams 55 may correspond to the stitching along the lower side seams 43 in the embodiment of FIGS. 1-5 in that it extends through the front wall 29b, the back wall 27b, and the bandage 13b. Reinforcing tape (not shown) similar to the reinforcing tape 45 (FIG. 4) may be used along the seams 55, if desired. The stitching along the seams 37b, 39b, 41b and 43b may be identical to the corresponding stitching described with reference to FIGS. 1-5.

Each of the containers 47b may be identical to the container 47 (FIGS. 1-5) except that the formers smaller and adapted to fit within one of the compartments 33b.

Another difference between the pockets 17 and 17b is that the latter is longer and narrower. The reduced width of the pocket 17b is merely illustrative and not essential. The reduced width of the pocket 17b provides an uncovered upper marginal region 57 of the bandage 13b and the lower edge of the pocket is substantially flush with the side edge 21b. The increased length of the pocket 17b permits additional containers 47b of refrigerant gel 49b to be inserted into the pocket. Although the pocket 17b is long and although the refrigerant gel 49b may be solid, the regions along the seams 55 intermediate adjacent compartments 33b form hinges with permit the therapeutic wrap 11b to be wrapped around an injured region.

The therapeutic wrap 11b can be used in the manner described above with reference to the therapeutic wrap 11 except that the therapeutic wrap 11b is particularly adapted for use on larger areas of the body. By selecting the compartments 33b in which a container 47b of refrigerant gel 49b is inserted, the cooling action can be obtained precisely at the desired location.

Although exemplary embodiments of this invention have been shown and described, many changes, modifications and substitutions may be made by one with ordinary skill in the art without necessarily departing from the spirit and scope of this invention.

I claim:

1. A therapeutic wrap comprising:
    an elongated flexible bandage, said bandage being resilient in at least one direction and having first and second faces, said bandage being adapted to be wrapped around an injured region to resiliently compressively load the injured region;
    a pocket having a front wall, at least a substantial portion of said front wall being defined by means other than said bandage, said bandage being substantially longer than said pocket;
    means for attaching the pocket to the bandage with a substantial length of the bandage extending beyond said pocket;
    a refrigerant gel package including refrigerant gel and container means for containing the refrigerant gel therein; and
    said refrigerant gel package being carried by said pocket whereby the pocket and the refrigerant gel package are both carried by said bandage and said bandage can be wrapped around an injured region to resiliently compressively load the injured region.

2. A therapeutic wrap as defined in claim 1, wherein said pocket includes a back wall overlying the first face of said bandage, said refrigerant gel package is receivable between said front wall and said back wall, and said front wall and said back wall insulate the refrigerant gel package from the injured region.

3. A therapeutic wrap as defined in claim 2 wherein said pocket is openable, said attaching means includes stitching for joining the pocket to the bandage, and said bandage has first and second side edges and said pocket is no wider than about the distance between the side edges at said pocket.

4. A therapeutic wrap as defined in claim 3 wherein said refrigerant gel is pliable at temperatures down to about 5° Fahrenheit and said container means and said pocket are flexible.

5. A therapeutic wrap as defined in claim 1 wherein said container means includes a plurality of containers with each of said containers having some of the refrigerant gel therein and said pocket includes means defining individual compartments arranged along the length of the bandage at least some of the containers being in at least some of the compartments, respectively, the regions of the therapeutic wrap between adjacent compartments defining hinges which permit relative movement of the compartments.

* * * * *